United States Patent [19]

Van Gorp et al.

[11] Patent Number: 4,757,056

[45] Date of Patent: Jul. 12, 1988

[54] METHOD FOR TUMOR REGRESSION IN RATS, MICE AND HAMSTERS USING HEXURONYL HEXOSAMINOGLYCAN-CONTAINING COMPOSITIONS

[75] Inventors: Cornelius L. Van Gorp, Lebanon; Thomas M. Wolf, West Chester, both of Ohio

[73] Assignee: Hepar Industries, Inc., Franklin, Ohio

[21] Appl. No.: 727,565

[22] Filed: Apr. 26, 1985

Related U.S. Application Data

[63] Continuation-in-part of Ser. No. 586,047, Mar. 5, 1984, abandoned.

[51] Int. Cl.[4] ................. A61K 31/715; A61K 31/725; A61K 31/56

[52] U.S. Cl. ........................................ 514/54; 514/56; 514/171

[58] Field of Search ............................ 514/54, 56, 171

[56] References Cited

U.S. PATENT DOCUMENTS 4,230,699 10/1980 Fussi et al. ............................ 514/54

*Primary Examiner*—Jerome D. Goldberg

*Attorney, Agent, or Firm*—Kevin M. Foley

[57] ABSTRACT

Regression of established malignant tumors in rats, mice and hamsters is achieved with a combination of the heparin fragment hexuronyl hexosaminoglycan sulfate (HHS) together with a steroid such as hydrocortisone. HHS is clinically useful for its antineoplastic, inhibiting effects in tumor systems in rats, mice and hamsters.

4 Claims, No Drawings

METHOD FOR TUMOR REGRESSION IN RATS, MICE AND HAMSTERS USING HEXURONYL HEXOSAMINOGLYCAN-CONTAINING COMPOSITIONS

CROSS-REFERENCE TO RELATED APPLICATIONS

This application is a continuation-in-part of our earlier application Ser. No. 586,047 filed Mar. 5, 1984, now abandoned.

BACKGROUND OF THE INVENTION

This invention relates generally to the treatment of tumors in rats, mice and hamsters and more specifically to pharmaceutical compositions and methods effective in causing regression of established malignant tumors in rats, mice and hamsters. The compositions of the invention include the heteropolysaccharide hexuronyl hexosaminoglycan sulfate, hereinafter for convenience HHS, together with a cortisone derivative, typically hydrocortisone administered. Each component is in an amount and frequency needed to achieve the requisite degree of antineoplastic activity and tumor regression in rats, mice and hamsters. Preferably the degree of tumor regression achieved is sufficient to prevent metastases.

The use of heparin or a non-anticoagulant, low molecular weight heparin fragment (hexasaccharide having a relative molecular weight of about 2,000 Daltons) administered with cortisone to inhibit angiogenesis, regression of large tumor masses, and prevention of metastases is reported in a research article by Folkman et al, "Angiogenesis Inhibition and Tumor Regression Caused by Heparin or a Heparin Fragment in the Presence of Cortisone", *Science*, 719–724 (1983). The article describes the use of heparin and relatively low molecular weight heparin fragments which, when administered orally, resulted in the release of heparin fragments in the blood serum. The most effective fragment was a hexasaccharide with a molecular weight of about 1,600 Daltons. The investigators reported the angiogenesis inhibiting activity in the presence of cortisone varied greatly among manufacturers and that the anticoagulant function of heparin is not responsible for the inhibition of angiogenesis. Variance in heparin activity was responsible for selective activity in causing regression of only certain tumor tissues.

The need exists for a predictable, wide-spectrum therapy to enable one to achieve adequate tumor regression in rats, mice and hamsters.

DETAILED DESCRIPTION OF THE INVENTION

We have discovered and hereby disclose a method for effectively causing regression of established malignant tumors in rats, mice and hamsters requiring such treatment by administering heteropolysaccharide hexosaminoglycan sulfate (HHS) together with available steroids, their isomers or epimers. Pharmaceutical compositions, oral and parenteral dosage forms suitable for carrying out the method of the present invention are also disclosed.

Hexuronyl hexosaminoglycan sulfate (HHS) is used in the present invention is a purified product of a known, naturally occurring polysaccharide of the type described in U.S. Pat. No. 4,230,699 to Fussi et al and U.S. Pat. No. 4,264,733 also to Fussi et al; see also U.S. Pat. No. 4,143,132. The preferred hexuronyl hexosaminoglycan sulfate is in accordance with claim 1 of U.S. Pat. No. 4,230,699; see also the discussion beginning at line 33, column 2 of the same patent. HHS is described in these patents and elsewhere in the art as exhibiting anticoagulant, antithrombotic and clearing activities, suitable for either oral or parenteral administration. The discovery of these patents are hereby incorporated by reference.

The HHS used in accordance with the present invention consists is further characterized as follows:

Average Molecular Weight (viscosimetry) 25,000 Daltons minimum

Specific Rotation $-30°$ to $-70°$ $[\alpha]$ $D^{20}$

Hexosamines 26% minimum

Hexuronic Acid 24% minimum

Pharmaceutical presentation—The compositions according to the invention are conveniently in a form suitable for oral, rectal, parenteral or topical administration in a suitable pharmaceutical vehicle and in any case very well known generally for any particular kind of preparation. Thus for example tablets, capsules, ingestible liquid or powder preparations, creams and lotions for topical application, or suppositories, can be prepared as required. Injectable solutions are also within the ambit of the invention.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The quantity of HHS administered varies in accordance with a number of factors including the physical condition and tumor tissue involvement of the rat, mouse or hamster requiring treatment, the rat's, mouse's, or hamster's body weight and the regimen of treatment that is adopted. The amount of HHS is anticipated to be within the range of 50 mg to 5,000 mg per day with amounts in the range of at least 100 to 200 mg/day up to 0.5 to 2 grams/day being typical.

Method of treatment and pharmaceutical compositions in accordance with the present invention are assessed using art-recognized animal model studies as reported below. In the following examples all parts and percentages are by weight and all temperatures reported in degrees centigrade unless otherwise stated.

DESCRIPTION OF THE PREFERRED EMBODIMENTS

HHS has been tested to assess the pharmacological properties and its activity has been demonstrated. Two of the models used are virally induced new murine mammary adenocarcinomas, whereby metastatic tumors are transplated to the mammary gland of mice or rats.

All animals received the following solution orally:

| | |
|---|---|
| Hydrocortisone | 0.45 mg/ml |
| Tetracycline | 750 mg/ml |
| Bactrim | 50 mg/ml |

Selected animals received controlled amounts of Heparin sodium, U.S.P. manufactured by Hepar Industries, Inc., Franklin, Ohio (hepar), or by Abbott Laboratories, Inc. (panheparin) or HHS.

Model I

| | Tumor Volume in cmm after | | | |
|---|---|---|---|---|
| | 25 days | 30 days | 35 days | 40 days |
| Control | | 100 | | 450 |
| Panheparin (1000 u/ml) | 250 | 300 | 350 | 100 |
| Hepar (1000 u/ml) | 100 | 105 | 120 | 100 |
| HHS (5 mg/ml) | | 45 | | 25 |

Results indicate significant reduction in tumor volume using the HHS hydrocortisone combination treatment as compared with hepar and panheprin.

Model II

| | Tumor Volume in cmm after | | |
|---|---|---|---|
| | 12 days | 15 days | 20 days |
| No Treatment | 70 | 100 | 400 |
| Control | 75 | 100 | 210 |
| Panheparin (1000 u/ml) | 75 | 90 | 200 |
| HHS (5 mg/ml) | | 200 | 175 |

Model III

This pancreatic cancer model in hamsters was selected to evaluate the effectiveness of HHS on a soft tissue tumor with the following results:

| | No. of Animals | Tumor Growth Rate* | P-Value** |
|---|---|---|---|
| No treatment | 5 | .44 | — |
| Heparin alone | 5 | .39 | insignificant |
| Hepar + low dose hydrocortisone | 5 | .33 | .01 |
| Hepar + high dose hydrocortisone | 4 | .33 | .04 |
| HHS alone | 5 | .24 | .01 |
| HHS + low dose hydrocortisone | 5 | .34 | .01 |
| HHS + high dose hydrocortisone | 5 | .39 | insignificant |

*slope of regression line
**compared to no treatment

Interestingly, HHS alone significantly reduces tumor growth in hamsters possibly indicating that the steroids act as a catalyst or as an immune system repressant. On the contrary, HHS could also act as the endogenous stimulator of other inhibitors, although we do not wish to be bound to a particular theory of operation or activity.

Model IV

The efficacy of heparin (HEP), the heparin analogue hexuronyl hexosaminoglycan sulfate (HHS), and hydrocortisone (HC) in inhibiting the growth of pancreatic cancer was studied by an investigaror at the National Cancer Institute, National Institutes of Health, Bethesda, Md., USA. The model system chosen utilized 4 morphologically distinct pancreatic adenocarcinoma lines transplantable in Syrian hamster strains: CBP, LHP, LSP-3, and Pour-LVG. Syngeneic hamsters were inoculated with $LD_{100}$ doses of 1 of the 4 tumor lines and were randomly allocated to groups of 5 animals which received continuously in their drinking water: HEP (100 U/ml), HHS (10 mg/ml) alone, HC (0.5 mg/ml alone, HEP+HC, HHS+HC, or no additives (control.

Tumors were measured, growth rates calculated, and nonparametric statistical comparisons made among median growth rates of all groups. To confirm the capacity to produce angiogenesis factor, all tumors were tested in the rabbit cornea assay. In addition, tumors growing in treated animals were excised, and extracts were prepared for quantitative testing of in vitro angiogenesis in the Boyden Chamber bovine adrenal capillary endothelial cell migration assay.

All tumors produced angiogenesis in the rabbit cornea. No inhibition of tumor growth in any of the 4 tumor systems were observed, when compared to untreated with HC alone, HEP alone, HHS alone, or HEP+HC. Reduction in median tumor growth rate was observed in animals treated with HHS+HC bearing CBP ($p<0.05$), and LSP-3 ($p=0.06$) tumors, i.e, 3 of the 4 tumor lines used. Similarly, in vitro capillary cell migration was decreased by HHS+HC treatment in the CBP ($p<0.005$), Pour-LVG ($p<0.01$), and LSP-3 ($p<0.05$) models. LHP tumor showed no effect of HHS+HC treatment on tumor growth rate or on endothelial cell migration.

From these animal model studies, it may be concluded that when HHS is administered orally with HC, tumor growth in rats, mice and hamsters is inhibited in 3 of 4 transplantable pancreatic carcinoma lines, possibly through mechanisms inhibiting tumor angiogenesis in rats, mice and hamsters.

What is claimed is:

1. A method of causing regression of established malignant tumors in a rat, mouse or hamster, comprising administering to said rat, mouse or hamster an antineoplastic, tumor-regressing amount of hexuronyl hexosaminoglycan sulfate having an average molecular weight not less than 25,000 Daltons together with an effective amount of a steroid selected from the group consisting of cortisone, hydrocortisone and an isomer of epimer thereof.

2. The method of claim 1 in which the amount of hexuronyl hexosaminoglycan sulfate administered is an amount of about 50 to about 5,000 mg per day.

3. A pharmaceutical composition for causing the regression of established tumors comprising, in combination, a tumor-regressing amount of hexuronyl hexosaminoglycan sulfate together with an effective amount of cortisone, hydrocortisone or both in a pharmaceutically accepted carrier or diluent, wherein the average molecular weight of said hexuronyl hexosaminoglycan sulfate is not less than 25,000 Daltons.

4. The pharmaceutical composition of claim 3 in which the hexuronyl hexosaminoglycan sulfate is present in an amount of from 50 to about 5,000 mg.

* * * * *